United States Patent
Cortazar Perez et al.

(10) Patent No.: US 12,042,663 B2
(45) Date of Patent: Jul. 23, 2024

(54) ELECTROMEDICAL DEVICE FOR BLOOD CLOTTING AND TREATMENT OF ULCERS AND OTHER SKIN INJURIES IN HUMAN AND ANIMAL PATIENTS

(71) Applicant: ION BIOTEC, S.L., Ciudad Real (ES)

(72) Inventors: Osvaldo Daniel Cortazar Perez, Ciudad Real (ES); Ana Maria Megia Macias, Bilbao (ES)

(73) Assignee: MEDICAL PLASMAS, S.L., Noain (ES)

( * ) Notice: Subject to any disclaimer, the term of this patent is extended or adjusted under 35 U.S.C. 154(b) by 852 days.

(21) Appl. No.: 17/262,029

(22) PCT Filed: Jul. 2, 2019

(86) PCT No.: PCT/ES2019/000049
§ 371 (c)(1),
(2) Date: Jan. 21, 2021

(87) PCT Pub. No.: WO2020/021133
PCT Pub. Date: Jan. 30, 2020

(65) Prior Publication Data
US 2021/0282832 A1    Sep. 16, 2021

(30) Foreign Application Priority Data

Jul. 25, 2018  (ES) .......................... ES201800455U

(51) Int. Cl.
*A61N 1/44* (2006.01)
*A61L 2/00* (2006.01)
(Continued)

(52) U.S. Cl.
CPC .............. *A61N 1/44* (2013.01); *A61L 2/0011* (2013.01); *A61L 2/26* (2013.01); *H05H 1/466* (2021.05); *H05H 2245/34* (2021.05)

(58) Field of Classification Search
CPC ........ A61B 18/042; A61B 2018/00583; A61B 2018/00589; A61B 2018/00452;
(Continued)

(56) References Cited

U.S. PATENT DOCUMENTS

| | | | |
|---|---|---|---|
| 8,267,884 B1 * | 9/2012 | Hicks .................. | A61B 18/042 604/23 |
| 8,328,982 B1 * | 12/2012 | Babayan .............. | H05H 1/2406 156/345.43 |

(Continued)

OTHER PUBLICATIONS

Yong Cheol Hong, "Microplasma jet at atmospheric pressure", Article, 2006, 1-3, vol. 89, Applied Physics Letters.
(Continued)

*Primary Examiner* — Khadijeh A Vahdat
*Assistant Examiner* — Marina Delaney Templeton
(74) *Attorney, Agent, or Firm* — ArentFox Schiff LLP

(57) ABSTRACT

The proposed invention relates to an electromedical device that produces a cold plasma at atmospheric pressure for use in blood clotting and the treatment of ulcers and other skin injuries in human and animal patients. The main claims relate to the use of gas pre-treated by means of a cooling and dehumidification, together with a system of plasma expansion chambers in the outlet channel of same. As a result of these innovations, the plasma produced using the invention has a lower temperature than those in the prior art, preserving greater effectiveness both in blood clotting and in the disinfection and treatment of skin injuries, without causing any damage to the patient's healthy tissue. The device can be used in the treatment of human and animal patients to considerably accelerate blood clotting without damage to healthy tissue, during clinical and surgical treatments. I can also be used to treat ulcers and other skin injuries, owing to its disinfection properties, without damaging healthy tissue.

7 Claims, 2 Drawing Sheets

(51) Int. Cl.
*A61L 2/26* (2006.01)
*H05H 1/46* (2006.01)

(58) Field of Classification Search
CPC ........... H05H 2245/30; H05H 2245/32; H05H 2245/34; H05H 1/466; H05H 1/46; H05H 1/4645; A61L 2/0011; A61L 2/26; A61N 1/44

See application file for complete search history.

(56) References Cited

U.S. PATENT DOCUMENTS

| | | |
|---|---|---|
| 2009/0188626 A1 | 7/2009 | Lu et al. |
| 2011/0301412 A1* | 12/2011 | Cho .................. A61N 1/44 606/41 |
| 2012/0141321 A1 | 6/2012 | Merbahi et al. |
| 2012/0172874 A1* | 7/2012 | Fischer ............... A61B 18/042 606/49 |
| 2012/0187841 A1 | 7/2012 | Kindel et al. |
| 2014/0180276 A1 | 6/2014 | Kuo |
| 2016/0081745 A1* | 3/2016 | Rajagopalan ...... A61B 18/1492 606/41 |
| 2016/0181069 A1 | 6/2016 | Watson et al. |
| 2018/0085155 A1 | 3/2018 | Konesky et al. |

OTHER PUBLICATIONS

L. Bardos, "Cold atmospheric plasma: Sources, processes, and applications", Article, 2010, 6705-6713, vol. 518, Thin Solid Films.

\* cited by examiner

ELECTROMEDICAL DEVICE FOR BLOOD CLOTTING AND TREATMENT OF ULCERS AND OTHER SKIN INJURIES IN HUMAN AND ANIMAL PATIENTS

CROSS-REFERENCE TO RELATED APPLICATIONS AND PRIORITY

This patent application claims priority from PCT Patent Application No. PCT/ES2019/000049 filed Jul. 25, 2019, which claims priority from Spanish Patent Application No. U201800455 filed Jul. 2, 2018. Each of these patent applications are herein incorporated by reference in their entirety.

A61B18/10. Medical Science, Veterinary and hygiene. Diagnostics, Surgery, and identification.

A61D1/00. Medical Science, Veterinary and hygiene. Instruments, devices, tools, or veterinary methods. Veterinary instruments.

INVENTION BACKGROUND

In physics, plasma is defined as the fourth state of matter. It is obtained by delivering enough energy to a gas so that a significant part of its molecules or atoms ionize. There are many examples of plasmas in nature ranging from the northern lights and electrical discharges in storms to stars, whose corona is in that state. In addition, there are technological examples such as plasmas in fluorescent lighting tubes and plasma screens, among others. Thermal plasmas are those that are in thermodynamic equilibrium and are capable of transferring heat to any object with which they are put in contact. Thermal plasmas produced by electrical discharges at atmospheric pressure have been widely used for treating tissues in human and animal patients. Devices called "electric scalpels" use this type of plasmas and have been used in operating rooms for some decades. However, they produce extensive damage to the patient's tissue, inducing blood clotting by cauterization with the consequent death of the cellular tissue due to high temperatures and heat transfer to it. The negative consequence of the described method is that the recovery time of the patient is increased because the dead cells must be eliminated by the body and replaced by healthy cells as part of the healing process. The need to achieve methods that produce rapid coagulation without damaging healthy tissue has produced a series of developments based on the use of non-thermal plasmas at atmospheric pressure such as those proposed by Ximpei Lu in US 20090188626A1, Eckhard Kindel in US 20120187841A1, Gregory Konesky in US 2018085155A1 and Greg Watson at US2016181069A1, among others. All these inventions use the low heat transfer of non-thermal plasmas with other materials because they are out of thermodynamic equilibrium as their main characteristic. These plasmas are also called "Cold Atmospheric Plasmas" or by the acronym CAP. In addition, these non-thermal plasmas have the important property of killing bacteria and fungi without hardly affecting the healthy tissue of the patient. This is due to the difference in the cellular structure, specifically in its outer membrane, of these organisms with that of mammals. The high concentration of ions and free radicals is responsible for this selective effect, being one of the principles that makes these plasmas an emerging tool of great value for the fight against bacteria resistant to antibiotics. This second aspect of the application, in addition to the aforementioned blood coagulation, has opened the field of application of non-thermal plasmas in the treatment of dermatological lesions, especially those whose colonization by resistant bacteria transforms them into ulcers that remain for long periods of time without being capable of healing.

The invention proposed here is an innovative device that produces a cold plasma at atmospheric pressure to be used in blood coagulation, treatment of ulcers and other dermatological lesions. The innovations detailed in the claims are completely original and cause the plasma produced by the proposed invention to have a lower temperature than those corresponding to the prior state of the art, while maintaining great effectiveness both in blood coagulation and in disinfection and treatment of dermatological lesions.

EXPLANATION OF THE INVENTION

The present invention relates to an electromedical device for blood coagulation, the treatment of ulcers and other dermatological lesions. A key to the present invention is the use of a non-thermal cold plasma of air or other gas at atmospheric pressure that is produced by the device with an original method that justifies the request presented here. The invention produces a plasma at atmospheric pressure that is out of thermodynamic equilibrium, which implies that it does not transmit heat to the skin of the patient but, nevertheless, the ions and reactive free radicals present in the plasma have sufficient energy to accelerate the natural mechanisms of blood clotting and destroy bacteria and fungi, without damaging the healthy tissue of the patient.

The present invention has the following characteristics related to its application:

a. It is applied on bleeding wounds producing a very remarkable acceleration of the natural clotting of the blood without damaging the healthy tissue of the patient.

b. It is applied on the surface of ulcers and other dermatological lesions of the patient, eliminating a wide spectrum of bacteria and fungi that includes resistant bacteria.

c. The ionized particles that are part of the plasma act without damaging the healthy cells of the patient's tissue.

d. The active medium is a plasma of air or other partially ionized gas at atmospheric pressure that is projected onto the patient's tissue by means of a manual applicator designed for this purpose.

e. It does not produce resistance in bacteria.

f. It does not produce side effects.

g. It does not produce waste.

h. It does not use any drug.

The equipment is composed of a high-frequency electric power generating unit, a gas injection system, an air compressor that is the gas used to produce the plasma, an inert gas bottle in the event that it is used alone or mixed with air, a gas injector system, a gas and electric power transport hose, a manual applicator where the plasma is produced, a gas cooling system, a gas dehumidification system, a general digital control system and a user control touch screen. It is important to note at this point that the implementation of pretreatment systems that dehumidify and cool the gas are part of the innovations claimed here with respect to the current state of the art. In the case of using air as the feed gas by means of the air compressor, humidity control is of great importance. This factor has not been considered by other inventors despite having a great influence due to the amount of oxygen that is contributed to the plasma from the water vapor naturally contained in the air. Regarding the gas cooling system, its effect significantly changes the final temperature of the plasma jet, be it air, inert gas or a suitable mixture of both carried out by the gas injection system. Both gas pretreatment systems produce a very notable improvement in plasma generation reproducibility, quality, and stability. These factors help expand the range of usability and safety of the invention with both human and animal patients. Other important advances with respect to the state of the art are in the development of the manual applicator. The system is formed by a frustoconical positive electrode axially perforated at its vertex and facing a flat ground electrode also axially perforated. Between them, a high-frequency electrical discharge is established with the energy provided by the high-frequency generator unit, producing a plasma of the gas that flows between both electrodes through the mentioned perforations. The positive electrode is connected to a metallic flow exchange part whose function is to exchange the circulation of the gas and electrical flows. In this way, the gas coming from the injection system is conducted through the axial perforation of the positive electrode, increasing its speed, passing through the plasma volume through its sinus and expelling it through the hole of the flat ground electrode, entering an exit channel that leads to the outside and which is described in detail later. This geometry is an innovation from the state of the art and is reflected in the claims. The other inventors do not use a frustoconical hollow electrode with a hole in its axis through which the gas flows at high speed to form the plasma, on the contrary, they use a solid electrode to establish the discharge and the gas flows outside of it. This design has the advantage of producing a first stage of plasma cooling when the gas passes through the plasma during its formation. Once the plasma is introduced into the hole of the flat ground electrode, it begins its journey through an outlet channel to the outside. In this channel a system of plasma expansion chambers has been implemented, composed of an alternating series of axially perforated circular discs of two different concentric diameters. This structure causes that the diameter of the outlet channel of the hand applicator not to have a constant diameter. Therefore, the outlet channel alternately presents two diameters, one small and the other larger, in such a way that when the plasma passes through the aforementioned channel it encounters volumes where it expands, called plasma expansion chambers, which correspond to larger diameter discs. These expansion chambers produce a very notable cooling of the plasma due to two physical effects; one is its rapid expansion, and the other is the increase in conduction surface with respect to a constant diameter channel, which favors the evacuation of heat. The plasma expansion chamber system is a radical innovation that makes it possible to produce a completely new second stage of cooling in the state of the art, notably improving the performance of the invention with respect to the previous ones being part of the claims. The entire set of elements described above is kept in a coaxial centered position by means of tubes of insulating material. In addition, the system is surrounded by a threaded metal housing and fixed to the metal body of the hand applicator that is grounded. Finally, a removable metal sheath has been implemented at the end of the applicator that is fixed on the metal casing to make it easily sterilizable and it can be replaced for use with each patient, avoiding possible cross-contamination during clinical and surgical use. Both the metal casing, the metal body of the manual applicator and the removable metal cover are conveniently grounded, ensuring the safety of the operator and the patient against electric shocks. The removable metal sleeve is also a state-of-the-art innovation and is claimed as part of the claims.

The equipment is capable of being used in the treatment of human and animal patients to remarkably accelerate blood clotting without damaging healthy tissue during clinical and surgical treatments. In addition, it can also be used for the treatment of ulcers and other dermatological lesions due to its disinfection properties without causing damage to healthy tissue.

BRIEF DESCRIPTION OF THE DRAWINGS

To complete the description that is being made and to help a better understanding of the characteristics of the invention, a set of drawings is attached as an integral part of the description, where, with an illustrative and non-limiting nature, the following has been represented.

PREFERRED EMBODIMENT OF THE INVENTION

Figure 1:
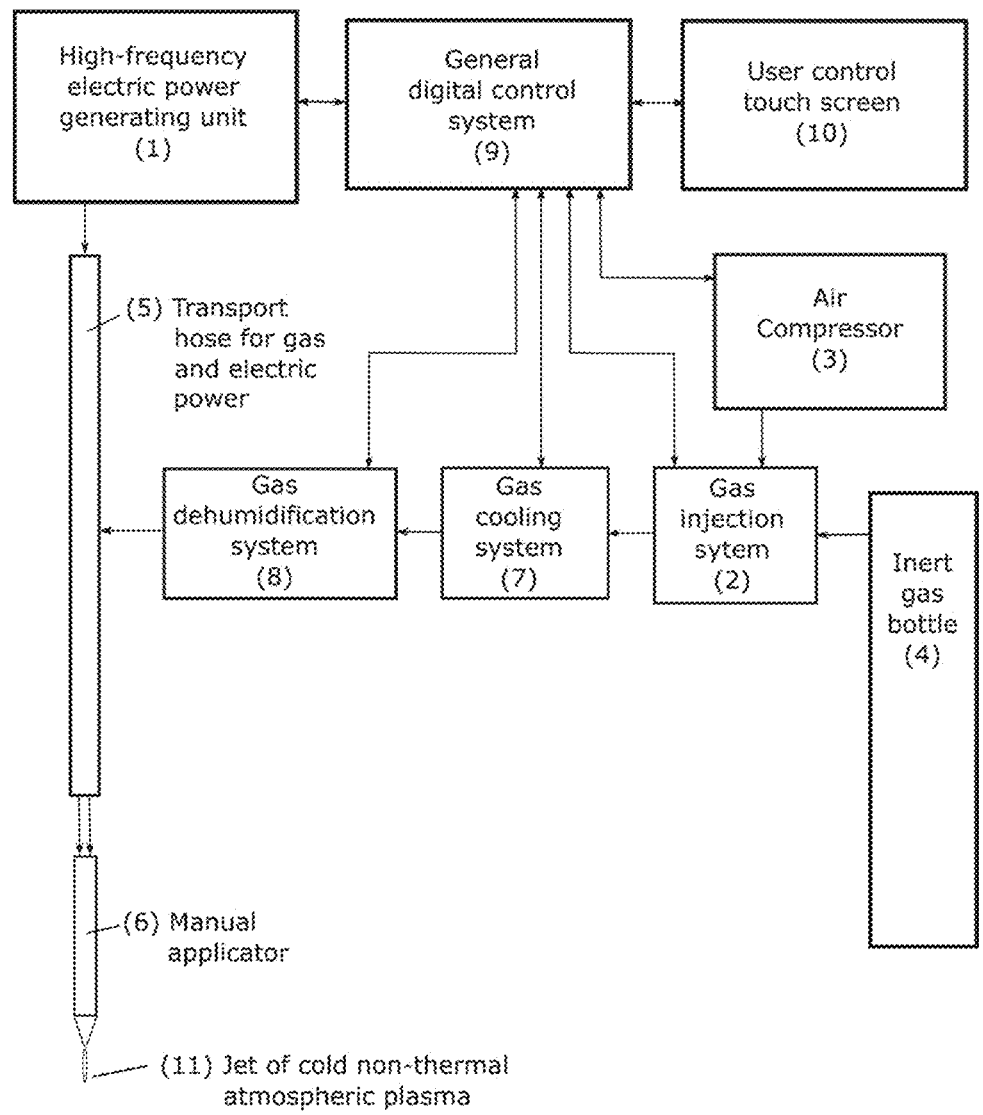
FIG. 1.—Shows a block diagram of the invention where the different conceptual parts that compose it and the way in which they are connected to each other can be appreciated. The arrows indicate the flow of matter, energy, or information as appropriate to each case, electricity, gas, and control signals.

An embodiment of the present invention is described below with the aid of FIGS. 1 and 2.

The proposed equipment comprises: a high-frequency electric power generating unit (1), a gas injection system (2), an air compressor (3), an inert gas bottle (4), a transport hose for gas and electric power (5), a manual applicator (6), a gas cooling system (7), a gas dehumidification system (8), a general digital control system (9), a touch screen of control for the user (10) and a jet of cold non-thermal atmospheric plasma of the gas used (11).

Figure 2:
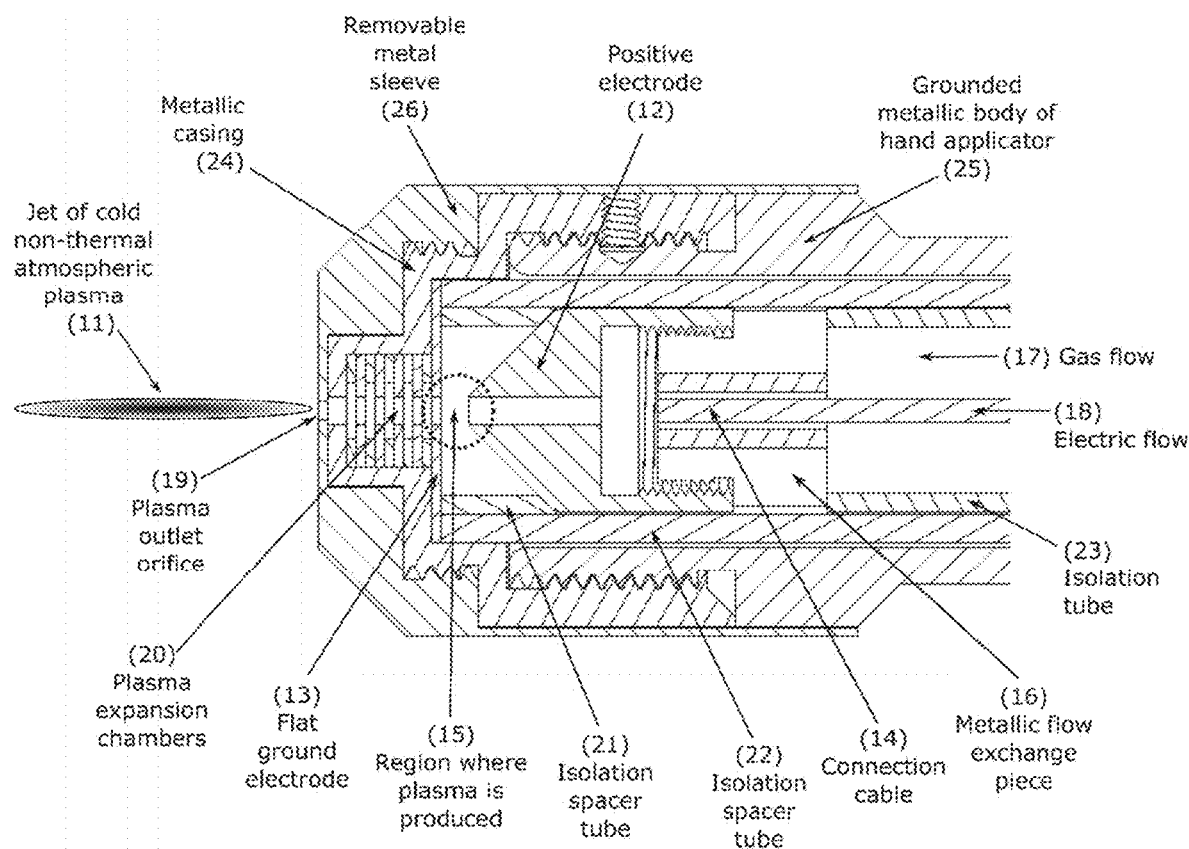
FIG. 2. Shows a cross-section view of the manual applicator where the different parts that make up can be seen. The whole system has cylindrical symmetry.

FIG. 2 shows in detail the structure of the hand applicator in a cross-section view. In general terms, the set has cylindrical symmetry where the different parts that compose it are coaxial. The system is formed by a positive electrode of a frustoconical shape axially perforated at its vertex (12) facing a flat ground electrode also axially perforated (13). Between them, a high frequency electric discharge is established with the energy provided by the generating unit (1) through the connection cable (14) that produces a plasma in the region that is indicated in FIG. 2 with a dotted circle (15). The positive electrode (12) is connected to a metallic flow exchange piece (16) whose function is to exchange the circulation of the gas flow (17) and the electrical one (18). In this way, the gas is conducted through the axial perforation of the positive electrode (12), increasing its speed, passing through the plasma volume through its sinus and being expelled through the plasma outlet orifice (19) from which the plasma jet (11) that will be used for the treatments is formed. In addition, between the region where the plasma is produced (15) and the plasma outlet orifice (19), a system of plasma expansion chambers (20) has been implemented, it is composed of an alternating series of axially perforated circular discs of two different concentric diameters. This structure causes that the diameter of the outlet channel that communicates the region where the plasma is produced (15) with the outlet orifice thereof (19) does not have a constant diameter. On the contrary, the outlet channel alternately has two diameters, one small and one large, in such a way that when the plasma passes through the channel, it encounters volumes where it expands, which are called plasma expansion chambers, and which correspond with larger diameter discs. The entire set of elements described above is kept in a coaxial centered position by means of tubes of insulating material (21), (22) and (23). Furthermore, the system is surrounded by a metallic casing (24) threaded and fixed to the metallic body of the grounded hand applicator (25). Finally, a removable metal cover (26) has been implemented, it is fixed on the metal casing (24) in a way that allows it to be easily sterilizable and replaced for use with each patient, avoiding possible cross contamination during clinical and surgical use. Both the metal casing (24), the metal body of the manual applicator (25) and the removable metal sleeve (26) are conveniently connected to ground, guaranteeing the safety of the operator and the patient with respect to electric shocks.

Once the gas flow (17) from the gas injection system (2) has been established, it is treated by the gas pretreatment systems (7) and (8), entering the transport hose (5) and heading towards the hand applicator (6). After a set time has elapsed to reach the appropriate humidity and temperature conditions in the gas, the high-frequency electrical energy generating unit (1) is activated, producing the plasma within the manual applicator (6) in the region (15) that corresponds with the free volume between the axially perforated frustoconical positive electrode (12) and the axially perforated flat ground electrode (13). The plasma is cooled and driven towards the outlet port (19) of the manual applicator (6) through a structure of alternating concentric rings of two different diameters that form a system of plasma expansion chambers (20). When the plasma passes through this structure, it undergoes a second cooling to finally emerge through the outlet orifice (19). From the moment in which the exit of the plasma is observed by the end of the manual applicator (6), the operator can use the system by applying the plasma jet (11) on the surface of the lesion or wound to be treated.

The invention claimed is:

1. An electromedical device for blood coagulation, treatment of ulcers and other dermatological lesions in human and animal patients comprising:
    an inert gas bottle or an inert gas tank,
    a gas injection system configured to extract an inert gas from the inert gas bottle or the inert gas tank and to provide a feed gas including a compressed air, the inert gas, or a combination thereof;
    an air compressor system connected to the gas injection system and configured to provide the compressed air,
    a gas cooling system connected to the gas injection system and configured to cool down the feed gas;
    a gas dehumidification system connected to the gas cooling system and configured to dehumidify the feed gas;
    a gas and electrical energy transport hose connected to the gas dehumidification system;
    a manual applicator connected to the gas and electrical energy transport hose and configured to apply a jet of a cold non-thermal plasma of the feed gas, or a partially ionized gas, at atmospheric pressure to a patient's tissue;
    a high-frequency electrical power generating unit for producing the cold non-thermal plasma of the feed gas or the partially ionized gas, by producing a high-frequency electrical discharge on the feed gas of the manual applicator; and
    a general digital control system connected to the gas injection system, the air compressor system, the gas cooling system, the gas dehumidification system, and the high-frequency electrical power generating unit and configured to control the gas injection system, the air compressor system, the gas cooling system, the gas dehumidification system and the high-frequency electrical power generating unit;
    wherein the manual applicator comprises:
        a frustoconical positive electrode axially having a vertex, wherein the frustoconical positive electrode is perforated at the vertex;
        a flat ground electrode axially perforated placed in front of the frustoconical positive electrode so that the high-frequency electrical discharge is established between the frustoconical positive electrode and the flat ground electrode, with an energy provided by the high-frequency electrical power generating unit, thereby defining a region where the cold non-thermal plasma of the feed gas or the partially ionized gas is produced,
        a metallic flow exchange part connected to the frustoconical positive electrode to exchange a circulation of the feed gas and the high-frequency electrical discharge; and
        an exit channel that leads to an outside of the manual applicator and is connected to the flat ground electrode,
    wherein the feed gas coming from the gas injection system passes through a sinus of the region where the cold non-thermal plasma of the feed gas or the partially ionized gas is produced and expels the cold non-thermal plasma of the feed gas or the partially ionized gas through a hole of the flat ground electrode and through the exit channel.

2. The electromedical device according to claim 1, comprising a user control touch screen connected to the general digital control system for introducing control commands.

3. The electromedical device according to claim 1, wherein the exit channel comprises a plasma outlet orifice and a system of plasma expansion chambers[,] placed between the flat ground electrode and the plasma outlet orifice and composed of an alternating series of axially perforated circular discs of two different concentric diameters, so that the cold non-thermal plasma of the feed gas or the partially ionized gas expands on passing through the system of plasma expansion chambers, producing a cooling of the cold non-thermal plasma of the feed gas or the partially ionized gas.

4. The electromedical device according to claim 1, comprising at least one tube of insulating material for keeping one or more of the frustoconical positive electrode or the metallic flow exchange part in a coaxial centered position, a grounded hand applicator surrounding the frustoconical positive electrode, the flat ground electrode, and the metallic flow exchange part, and a metallic casing threaded and fixed to a metallic body of the grounded hand applicator.

5. The electromedical device according to claim 4, comprising a removable metal cover fixed on the metallic casing and being sterilizable and replaceable.

6. The electromedical device according to claim 4, wherein the metallic casing, the metallic body of the grounded hand applicator, and a removable metal sleeve are configured to be connected to ground.

7. A method for blood coagulation, treatment of ulcers and dermatological lesions by a manual applicator, comprising the steps of:
    extracting an inert gas from an inert gas bottle with a gas injection system;
    providing a compressed air with an air compressor system connected to the gas injection system;

providing, via the gas injection system, a feed gas including a compressed air, the inert gas, or a combination thereof;

cooling down the feed gas coming from the gas injection system using a gas cooling system to provide a cooled gas;

controlling a moisture of the cooled gas with a gas dehumidification system to provide a dehumidified gas;

transporting the dehumidified gas with a gas and electrical energy transport hose;

producing a cold non-thermal plasma of the dehumidified gas or a partially ionized gas by producing a high-frequency electrical discharge on the dehumidified gas using a high-frequency electrical power generating unit; and applying a jet of the cold non-thermal plasma of the dehumidified gas or the partially ionized gas at atmospheric pressure to a patient's tissue with the manual applicator;

wherein the manual applicator comprises:
 a frustoconical positive electrode axially having a vertex, wherein the frustoconical positive electrode is perforated at the vertex;
 a flat ground electrode axially perforated placed in front of the frustoconical positive electrode so that the high-frequency electrical discharge is established between the frustoconical positive electrode and the flat ground electrode, with an energy provided by the high-frequency electrical power generating unit, thereby defining a region where the cold non-thermal plasma of the dehumidified gas or the partially ionized gas is produced,
 a metallic flow exchange part connected to the frustoconical positive electrode to exchange a circulation of the dehumidified gas and the high-frequency electrical discharge; and
 an exit channel that leads to an outside of the manual applicator and is connected to the flat ground electrode, wherein the dehumidified gas coming from the injection system passes through a sinus of the region where the cold non-thermal plasma of the dehumidified gas or the partially ionized gas is produced and expels the cold non-thermal plasma of the dehumidified gas or the partially ionized gas through a hole of the flat ground electrode and through the exit channel.

* * * * *